United States Patent
Dai et al.

(10) Patent No.: US 10,087,190 B1
(45) Date of Patent: Oct. 2, 2018

(54) LACTONES

(71) Applicant: Purdue Research Foundation, West Lafayette, IN (US)

(72) Inventors: Mingji Dai, West Lafayette, IN (US); Mohamed Seleem, West Lafayette, IN (US); Xianglin Yin, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/949,124

(22) Filed: Apr. 10, 2018

Related U.S. Application Data

(60) Provisional application No. 62/488,884, filed on Apr. 24, 2017.

(51) Int. Cl.
*C07D 491/048* (2006.01)
*C07D 491/20* (2006.01)
*C07D 405/04* (2006.01)

(52) U.S. Cl.
CPC ....... *C07D 491/048* (2013.01); *C07D 405/04* (2013.01); *C07D 491/20* (2013.01)

(58) Field of Classification Search
CPC .......................... C07D 491/048; C07D 491/20
USPC .......................................................... 548/453
See application file for complete search history.

(56) References Cited

U.S. PATENT DOCUMENTS

| | | | | |
|---|---|---|---|---|
| 7,799,791 B2* | 9/2010 | Quibell | ............... | C07D 491/04 435/23 |
| 8,389,737 B2* | 3/2013 | Quibell | ............... | C07D 491/04 548/159 |
| 2008/0234260 A1* | 9/2008 | Nilsson | ............... | A61K 31/407 514/233.8 |
| 2009/0023747 A1* | 1/2009 | Tickle | ............... | C07D 471/04 514/254.02 |

OTHER PUBLICATIONS

Miyazaki et al. "Studies on the Structure of the Active Principle of Digenea simplex Ag" Yakugaku Zasshi (1954), 74, 215-216. (Year : 1954).*
Rokack et al. Journal of the Chemical Society [Section D]: Chemical Communications (1971), (18), 1085-1086. (Year: 1971).*

* cited by examiner

*Primary Examiner* — Nyeemah A Grazier
(74) *Attorney, Agent, or Firm* — Purdue Research Foundation; Zhigang Rao

(57) ABSTRACT

The present disclosure relates to novel lactones such as dihydropyrrole-fused furanones, a novel palladium-catalyzed carbonylation method to make the novel lactones, and method of using the novel lactones as anti-fungal and/or anti-bacteria agents.

5 Claims, No Drawings

LACTONES

CROSS-REFERENCE TO RELATED APPLICATION

The present U.S. patent application is related to and claims the priority of U.S. Provisional Application Ser. No. 62/488,884, filed Apr. 24, 2017, the contents of which are hereby incorporated by reference in its entirety into this application.

GOVERNMENT RIGHTS

This invention was made with government support under National Science Foundation Career Award No. 1553820 awarded by National Science Foundation. The United States government has certain rights in the invention.

TECHNICAL FIELD

The present disclosure relates to novel lactones such as dihydropyrrole-fused furanones, a novel palladium-catalyzed carbonylation method to make the novel lactones, and method of using the novel lactones.

BACKGROUND

This section introduces aspects that may help facilitate a better understanding of the disclosure. Accordingly, these statements are to be read in this light and are not to be understood as admissions about what is or is not prior art.

Invasive fungal infections are a serious cause of mortality in many patients including an increasing number of immunocompromised patients. Few treatment choices exist and first-line therapies have significant limitations due to safety problem and lack of broad spectrum activity.

Novel antibacterial and antifungal agents and the efficient methods of making the agents are therefore needed.

SUMMARY

The present invention provides compounds with novel structures that may possess one or more of the following activities: antibacterial, antifungal, antiviral, anticancer, and antiparasitic activity. Specifically, the compounds of the present invention are represented in Formula I and Formula II below:

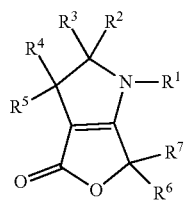

I or any salt thereof, wherein either $R^1$-$R^7$ are all hydrogen or at least one of $R^1$-$R^7$ is not hydrogen.

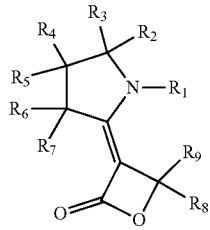

II or any salt thereof, wherein either $R^1$-$R^9$ are all hydrogen or at least one of $R^1$-$R^9$ is not hydrogen.

In one embodiment, the present disclosure provides palladium-catalyzed aminocarbonylative lactonization method of making compounds of Formula I and/or Formula II.

In one embodiment, the present disclosure provides methods of using compounds of Formula I and/or Formula II as anti-bacterial and/or anti-fungal agents.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents, that can be bonded to a substituted carbon (or other such as nitrogen) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, (CH$_2$)$_{0-2}$P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The terms "halo," "halogen," or "halide" group, as used herein, by themselves or as part of another substituent, mean, unless otherwise stated, a fluorine, chlorine, bromine, or iodine atom. The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

As used herein, the term "salts" and/or "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

As used herein, the term "nitrogen-protecting group" in the present disclosure may be any functional group that can make the amine nitrogen to be protected as any form of carbamate, benzyl amine, amide, thioamide, sulfonamide, urea, or thiourea. The nitrogen-protecting group may include but is not limited to benzoyl, benzyloxycarbonyl, t-butoxycarbonyl, benzene sulfonyl, toluene sulfonyl, benzyl, benzhydryl, trityl, acetyl, or trifluoroacetyl.

The present invention provides certain novel compounds that are anti-bacteria and/or anti-fungal agents. Accordingly, the present invention provides a compound of Formula I:

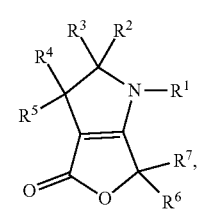

or any salt thereof, wherein either $R^1$-$R^7$ are all hydrogen or at least one of $R^1$-$R^7$ is not hydrogen.

In one embodiment, the present invention provides a compound of Formula I, wherein $R^1$ is H, C1-C8 straight or branched alkyl, C3-C8 cycloalkyl, C6-C10 aryl, C4-C10 heteroaryl, hydroxyl, C1-C6 straight or branched alkoxyl, —C(X)—$R^{10}$, —C(X)—$OR^{11}$, —$SO_2R^{12}$, —C(X)$NR^{13}R^{14}$, or a nitrogen-protecting group, wherein the alkyl, aryl or heteroaryl is optionally substituted with one or more —$NO_2$, halogen, $CF_3$, or phenyl;

$R^2$, $R^3$, $R^4$, and $R^5$ are independently H, C1-C8 straight or branched alkyl, C3-C8 cycloalkyl, C6-C10 aryl, C4-C10 heteroaryl, hydroxyl, halogen, or C1-C6 straight or branched alkoxyl, wherein the alkyl, aryl or heteroaryl is optionally substituted with one or more —NO$_2$, halogen, CF$_3$, or phenyl;

R$^6$, R$^7$ are independently H, C1-C8 straight or branched alkyl, C3-C8 cycloalkyl, C6-C10 aryl, C4-C10 heteroaryl, C1-C6 straight or branched alkoxyl, wherein R$^6$, R$^7$ may form a C3-C10 carbon ring or heterocyclic ring comprising N, O, or S, and when the heterocyclic formed by R$^6$ and R$^7$ has N, the N is optionally attached to C1-C8 straight or branched alkyl, C3-C8 cycloalkyl, C6-C10 aryl, C4-C10 heteroaryl, —C(X)—R$^{10}$, —C(X)—OR$^{11}$, —SO$_2$R$^{12}$, —C(X)NR$^{13}$R$^{14}$, or a nitrogen-protecting group;

R$^1$-R$^{14}$ are independently H, C1-C8 straight or branched alkyl, C3-C8 cycloalkyl, C6-C10 aryl, C4-C10 heteroaryl, wherein the alkyl, aryl, or heteroaryl is optionally substituted with one or more C1-C4 straight or branched alkyl, —NO$_2$, halogen, or CF$_3$; and X is O or S.

In another embodiment, the present invention provides a compound of Formula I wherein R$^1$ is selected from the group consisting of H, C1-C4 straight or branched alkyl, C3-C8 cycloalkyl, —C(O)—R$^{10}$, —C(O)—OR$^{11}$, —SO$_2$R$^{12}$, —C(O)NR$^{13}$R$^{14}$, and a nitrogen-protecting group, wherein the alkyl is optionally substituted with one or more —NO$_2$, halogen, CF$_3$, or phenyl;

R$^2$, R$^3$, R$^4$, and R$^5$ are independently selected from the group consisting of H, C1-C4 straight or branched alkyl, hydroxyl, halogen, and C1-C4 straight or branched alkoxyl;

R$^6$, R$^7$ are independently selected from the group consisting of H, C1-C8 straight or branched alkyl, C3-C8 cycloalkyl, C6-C10 aryl, C4-C10 heteroaryl, C1-C6 straight or branched alkoxyl, wherein R$^6$, R$^7$ may form a C3-C10 carbon ring or heterocyclic ring comprising N, O, or S, and when the heterocyclic formed by R$^6$ and R$^7$ has N, the N is optionally attached to C1-C4 straight or branched alkyl, C3-C8 cycloalkyl, C6-C10 aryl, C4-C10 heteroaryl, —C(O)—R$^{10}$, —C(O)—OR$^{11}$, —SO$_2$R$^{12}$, —C(O)NR$^{13}$R$^{14}$, and a nitrogen-protecting group; and R$^{10}$-R$^{14}$ are independently H, C1-C4 straight or branched alkyl, C3-C8 cycloalkyl, C6-C10 aryl, C4-C10 heteroaryl, wherein the alkyl, aryl, or heteroaryl is optionally substituted with one or more C1-C4 straight or branched alkyl, —NO$_2$, halogen, or CF$_3$.

In one embodiment, the present invention provides a compound of Formula II:

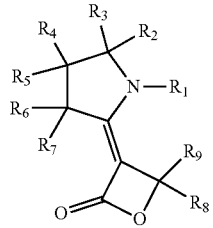

II or any salt thereof, wherein either R$^1$-R$^9$ are all hydrogen or at least one of R$^1$-R$^9$ is not hydrogen.

In one embodiment, the present invention provides a compound of Formula II, wherein R$^1$ is H, C1-C8 straight or branched alkyl, C3-C8 cycloalkyl, C6-C10 aryl, C4-C10 heteroaryl, hydroxyl, C1-C6 straight or branched alkoxyl, —C(X)—R$^{10}$, —C(X)—OR$^{11}$, —SO$_2$R$^{12}$, —C(X)NR$^{13}$R$^{14}$, or a nitrogen-protecting group, wherein the alkyl, aryl or heteroaryl is optionally substituted with one or more —NO$_2$, halogen, CF$_3$, or phenyl;

R$^2$, R$^3$, R$^4$, R$^5$, R$^6$, and R$^7$ are independently H, C1-C8 straight or branched alkyl, C3-C8 cycloalkyl, C6-C10 aryl, C4-C10 heteroaryl, hydroxyl, halogen, or C1-C6 straight or branched alkoxyl, wherein the alkyl, aryl or heteroaryl is optionally substituted with one or more —NO$_2$, halogen, CF$_3$, or phenyl;

R$^8$, R$^9$ are independently H, C1-C8 straight or branched alkyl, C3-C8 cycloalkyl, C6-C10 aryl, C4-C10 heteroaryl, C1-C6 straight or branched alkoxyl, wherein R$^8$, R$^9$ may form a C3-C10 mono or bicyclic carbon ring or heterocyclic ring comprising N, O, or S, and when the heterocyclic formed by R$^8$ and R$^9$ has N, the N is optionally attached to C1-C8 straight or branched alkyl, C3-C8 cycloalkyl, C6-C10 aryl, C4-C10 heteroaryl, or a nitrogen-protecting group;

R$^{10}$-R$^{14}$ are independently H, C1-C8 straight or branched alkyl, C3-C8 cycloalkyl, C6-C10 aryl, C4-C10 heteroaryl, wherein the alkyl, aryl or heteroaryl is optionally substituted with one or more C1-C4 straight or branched alkyl, —NO$_2$, halogen, or CF$_3$, and X is O or S.

In another embodiment, the present invention provides a compound of Formula II, wherein R$^1$ is selected from the group consisting of H, C1-C4 straight or branched alkyl, C3-C8 cycloalkyl, —C(O)—R$^{10}$, —C(O)—OR$^{11}$, —SO$_2$R$^{12}$, —C(O)NR$^{13}$R$^{14}$, and a nitrogen-protecting group, wherein the alkyl is optionally substituted with one or more —NO$_2$, halogen, CF$_3$, or phenyl;

R$^2$-R$^7$ are independently selected from the group consisting of H, C1-C4 straight or branched alkyl, hydroxyl, halogen, and C1-C4 straight or branched alkoxyl;

R$^8$, R$^9$ are independently selected from the group consisting of H, C1-C8 straight or branched alkyl, C3-C8 cycloalkyl, C6-C10 aryl, C4-C10 heteroaryl, C1-C6 straight or branched alkoxyl, wherein R$^8$, R$^9$ may form a C3-C10 carbon ring or heterocyclic ring comprising N, O, or S, and when the heterocyclic formed by R$^8$ and R$^9$ has N, the N is optionally attached to C1-C4 straight or branched alkyl, C3-C8 cycloalkyl, C6-C10 aryl, C4-C10 heteroaryl, —C(O)—R$^{10}$, —C(O)—OR$^{11}$, —SO$_2$R$^{12}$, —C(O)NR$^{13}$R$^{14}$, and a nitrogen-protecting group; and R$^{10}$-R$^{14}$ are independently H, C1-C4 straight or branched alkyl, C3-C8 cycloalkyl, C6-C10 aryl, C4-C10 heteroaryl, wherein the alkyl, aryl, or heteroaryl is optionally substituted with one or more C1-C4 straight or branched alkyl, —NO$_2$, halogen, or CF$_3$.

In one embodiment, the present invention provides a compound selected from the group consisting of:

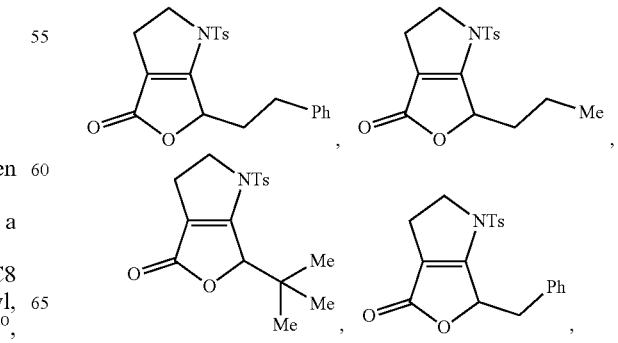

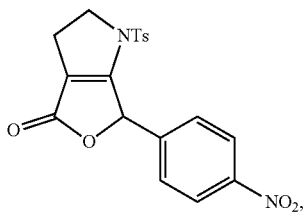

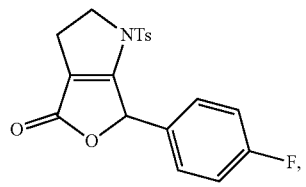

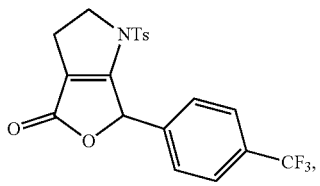

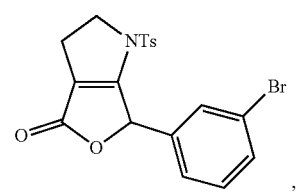

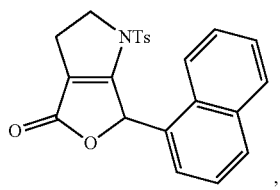

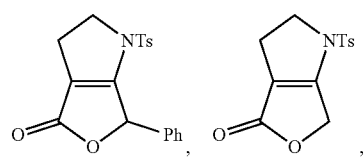

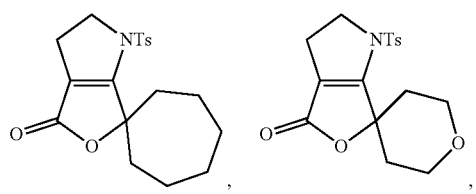

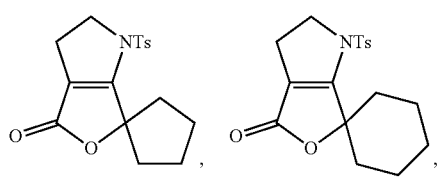

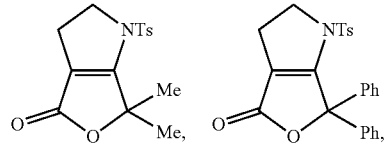

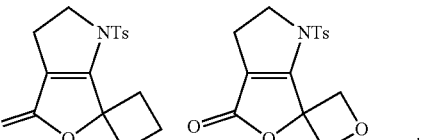

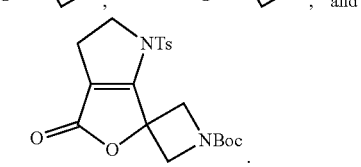

In one embodiment, the present invention provides a compound selected from the group consisting of:

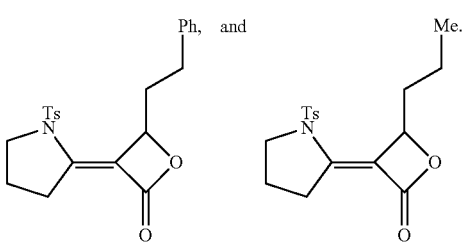 [SMILES: Cc1ccc(S(=O)(=O)N2CCC/C2=C2\C(=O)OC2CCc2ccccc2)cc1 ; CCCC1OC(=O)/C1=C1\CCCN1S(=O)(=O)c1ccc(C)cc1]

In one embodiment, the present invention provides a compound of Formula I as an anti-fungal and/or anti-bacteria agent.

In one embodiment, the present invention provides a compound of Formula II as an anti-fungal and/or anti-bacteria agent.

In one embodiment, the present invention provides a compound of Formula I as an inhibitor for *Clostridium difficile*.

In one embodiment, the present invention provides a compound of Formula I as an inhibitor for *Clostridium difficile* P8, *Clostridium difficile* BAA1870, *Clostridium difficile* P 20, *Clostridium difficile* P 7, *Clostridium difficile* P 21, or any combination thereof.

In one embodiment, the present invention provides a compound of Formula I as an inhibitor of strains of *Candida albicans, Candida glabrata, Candida krusei, Cryptococcus gattii, Cryptococcus neoformans, Aspergillus fumigatus, Aspergillus niger, Aspergillus brasiliensis*, or any combination thereof.

In one embodiment, the present invention provides a compound of Formula II as an inhibitor of strains of *Candida albicans, Candida glabrata, Candida krusei, Cryptococcus gattii, Cryptococcus neoformans, Aspergillus fumigatus, Aspergillus niger, Aspergillus brasiliensis*, or any combination thereof.

In one embodiment, the present invention provides a method of making the compound of Formula I in any embodiment of the present disclosure, wherein the method comprises reacting a compound of formula A with carbon monoxide, a palladium catalyst, a ligand, and an oxidant in a solvent to provide the compound of formula I:

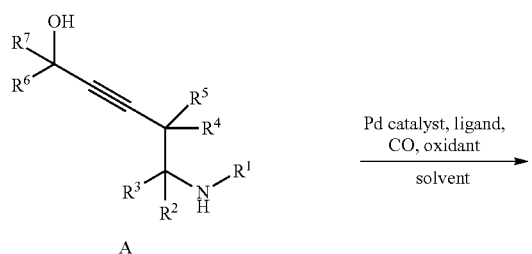

A

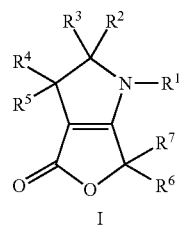

I wherein $R^1$-$R^{14}$ are defined in any embodiment for compound of formula I.

In one embodiment, the present invention provides a method of making the compound of Formula II in any embodiment of the present disclosure, wherein the method comprises reacting a compound of formula B with carbon monoxide, a palladium catalyst, a ligand, and an oxidant in a solvent to provide the compound of Formula II:

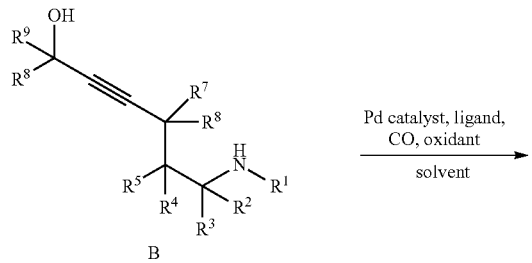

B

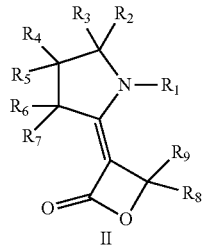

II wherein $R^1$-$R^{14}$ are defined in any embodiment for compound of Formula II.

The compounds of the present invention may be prepared by a variety of procedures, some of which are illustrated in the schemes below. Some substituents may be eliminated in the following schemes for the sake of clarity and are not intended to limit the teaching of the schemes in any way.

The method of preparing the compound of Formula I is illustrated in Scheme 1.

Scheme 1: The method of preparing the compound of Formula (I)

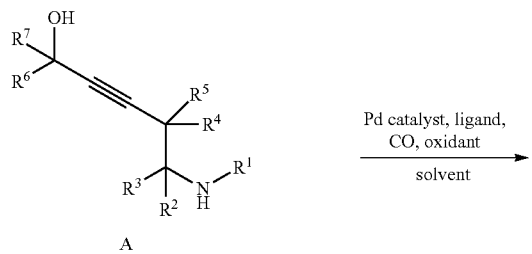

A

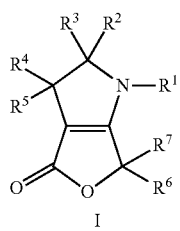

I

Compound A is reacted with carbon monoxide with a suitable palladium catalyst such as Pd(tfa)2 [palladium(II) trifluoroacetate], a suitable ligand such as 2,2-bipyridine, and a suitable oxidant such as p-benzoquinone, in a suitable solvent such as acetonitrile (MeCN) at a suitable temperature such as room temperature to provide the compound of Formula (I).

The method of preparing the compound of Formula II is illustrated in Scheme 2.

Scheme 2: The method of preparing the compound of Formula (II)

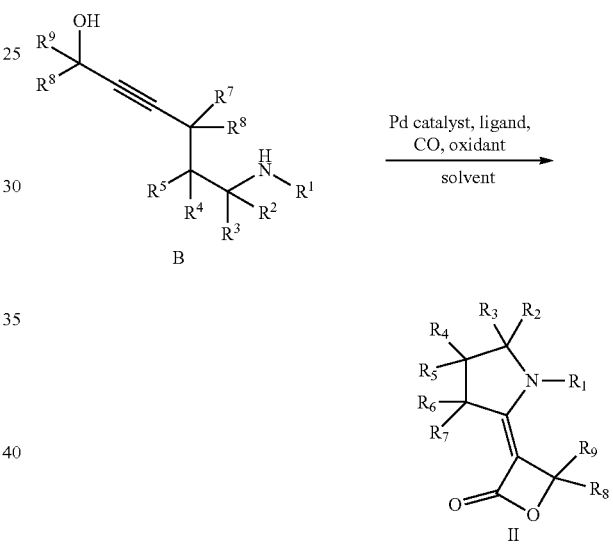

The reaction condition to prepare the compound of Formula II is essentially the same or similar to the preparation of the compound of Formula I except a different starting material with the Formula B is used. It was expected to achieve a fused six-membered ring to a five-membered ring based on the product of Formula I. However, the compound of Formula II is obtained as a novel scaffold which does not have a fused bicyclic rung system. Instead, a two-ring connected through a double bond is unexpectedly obtained.

The method of preparing the compound A and compound B are illustrated in Scheme 3 and Scheme 4.

Scheme 3: The method of preparing the compound A

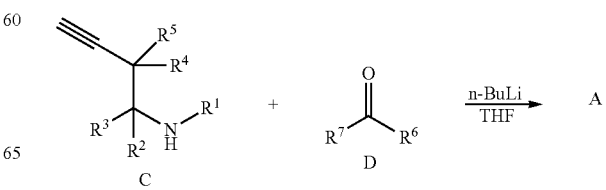

Scheme 4: The method of preparing the compound B

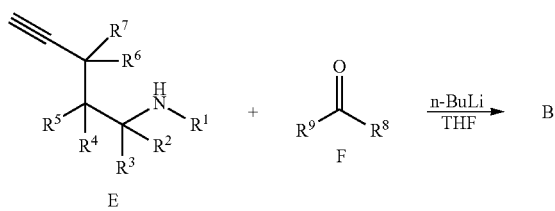

Compound C and D (Scheme 3) or E and F (Scheme 4) are reacted with a suitable base such as n-BuLi in a suitable solvent such as tetrahydrofuran (THF) to provide compound A or compound B. Compounds C, D, E and F are either commercial available or may be made by the methods known to skilled artisans.

The ligands that may be suitable for the reactions as disclosed in the present disclosure may include but is not limited to:

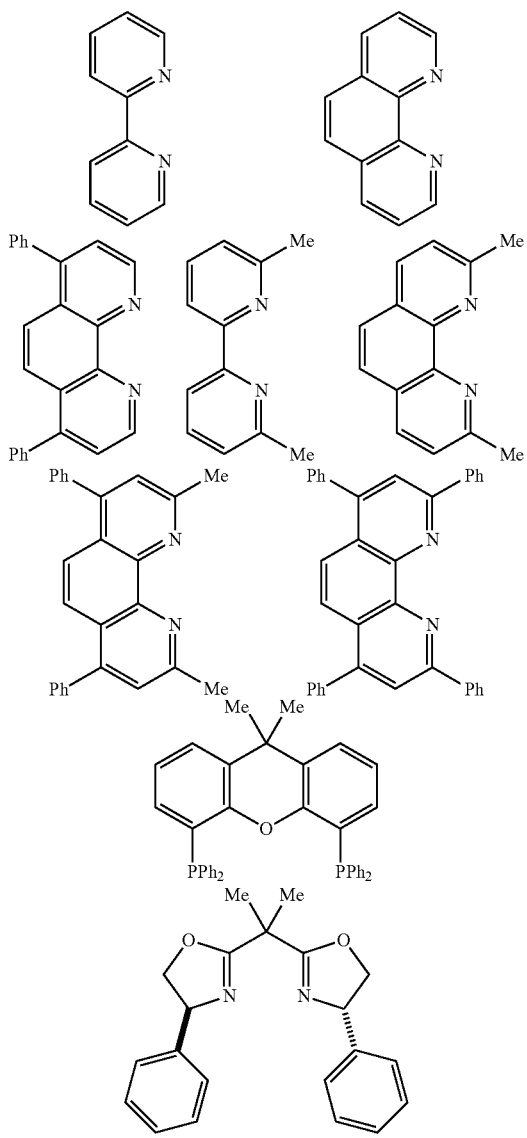

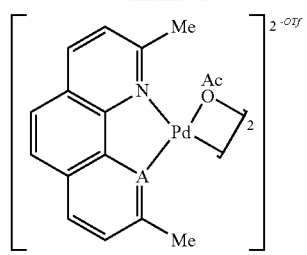

The oxidants that may be suitable for the reactions as disclosed in the present disclosure may include but is not limited to p-benzoquinone and 2,3-dichloro-5,6-dicyano-1,4-benzoquinone.

General Methods:

NMR spectra were recorded on Bruker spectrometers ($^1$H at 500 MHz and $^{13}$C at 125 MHz). Chemical shifts (δ) were given in ppm with reference to solvent signals [$^1$H NMR: CHCl$_3$ (7.26); $^{13}$C NMR: CDCl$_3$ (77.2)]. Column chromatography was performed on silica gel. All reactions sensitive to air or moisture were conducted under argon atmosphere in dry and freshly distilled solvents under anhydrous conditions, unless otherwise noted. Anhydrous THF was distilled over sodium benzophenone ketyl under Argon. Anhydrous CH$_2$Cl$_2$ was distilled over calcium hydride under Argon. Anhydrous MeCN was distilled over calcium hydride under Argon. All other solvents and reagents were used as obtained from commercial sources without further purification.

Preparations

Preparation 1: N-(5-hydroxy-7-phenylhept-3-yn-1-yl)-4-methylbenzenesulfonamide

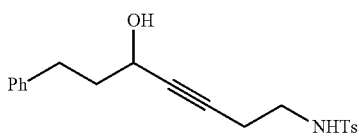

To a stirred solution of N-(but-3-yn-1-yl)-4-methylbenzenesulfonamide (112 mg, 0.50 mmol) in dry THF (5 mL), a 2.5 M solution of n-BuLi (0.39 mL, 0.98 mmol) in hexane was added dropwise at −78° C. over 10 min under argon atmosphere. The reaction mixture was allowed to react at the same temperature and stirred for a 1 h. Dissolved 3-phenyl-propanal (1.5 mmol) in 5 mL THF and added at −78° C. over 10 min to the previously formed mixture. The formed mixture was allowed to warmed up to room temperature and react for additional 1 h. The reaction was quenched by saturated NH$_4$Cl solution (5 mL) and extracted by EtOAc for 3 times. The organic layer was washed with brine, dried over Na$_2$SO$_4$ and concentrated under reduced pressure. The resulting residue was purified by flash chromatography (hexane/ethyl acetate=3/2) to provide Preparation 1 in 64% yield. HRMS (ESI), calcd for C$_{20}$H$_{23}$NO$_3$SNa [M+Na]$^+$ 380.1297, found 380.1280 m/z.

TABLE 1

Preparations 2-22 are prepared with essentially the same or similar method of preparing Preparation 1.

| Preparations | Structures | Chemical names | Physical Data [HRMS (ESI): m/z] [M + Na]+ |
|---|---|---|---|
| 2 | (structure) | N-(5-hydroxyoct-3-yn-1-yl)-4-methylbenzenesulfonamide | 318.1094 |
| 3 | (structure) | N-(5-hydroxy-6-phenylhex-3-yn-1-yl)-4-methylbenzenesulfonamide | 352.1004 |
| 4 | (structure) | N-(5-(4-fluorophenyl)-5-hydroxypent-3-yn-1-yl)-4-methylbenzenesulfonamide | 370.0929 |
| 5 | (structure) | N-(5-hydroxy-5-(4-(trifluoromethyl)phenyl)pent-3-yn-1-yl)-4-methylbenzenesulfonamide | 420.0786 |
| 6 | (structure) | N-(5-(3-bromophenyl)-5-hydroxypent-3-yn-1-yl)-4-methylbenzenesulfonamide | 430.0099 |
| 7 | (structure) | N-(5-hydroxy-5-(naphthalen-1-yl)pent-3-yn-1-yl)-4-methylbenzenesulfonamide | 402.1066 |
| 8 | (structure) | N-(5-hydroxy-5-phenylpent-3-yn-1-yl)-4-methylbenzenesulfonamide | 366.1105 |
| 9 | (structure) | N-(4-(1-hydroxycycloheptyl)but-3-yn-1-yl)-4-methylbenzenesulfonamide | 358.1405 |
| 10 | (structure) | N-(4-(4-hydroxytetrahydro-2H-pyran-4-yl)but-3-yn-1-yl)-4-methylbenzenesulfonamide | 346.1049 |

TABLE 1-continued

Preparations 2-22 are prepared with essentially the same or similar method of preparing Preparation 1.

| Preparations | Structures | Chemical names | Physical Data [HRMS (ESI): m/z] [M + Na]+ |
|---|---|---|---|
| 11 | 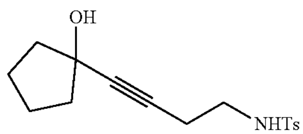 | N-(4-(1-hydroxycyclopentyl)but-3-yn-1-yl)-4-methylbenzenesulfonamide | 330.1099 |
| 12 | 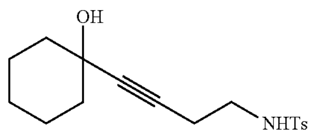 | N-(4-(1-hydroxycyclohexyl)but-3-yn-1-yl)-4-methylbenzenesulfonamide | 344.1228 |
| 13 | 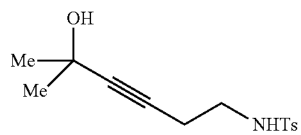 | N-(5-hydroxy-5-methylhex-3-yn-1-yl)-4-methylbenzenesulfonamide | 304.0950 |
| 14 | 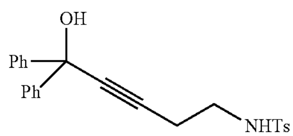 | N-(5-hydroxy-5,5-diphenylpent-3-yn-1-yl)-4-methylbenzenesulfonamide | 428.1320 |
| 15 | 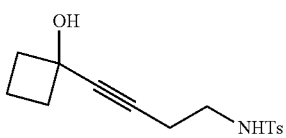 | N-(4-(1-hydroxycyclobutyl)but-3-yn-1-yl)-4-methylbenzenesulfonamide | 314.0950 |
| 16 | 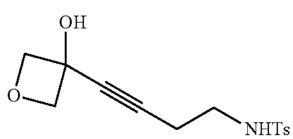 | N-(4-(3-hydroxyoxetan-3-yl)but-3-yn-1-yl)-4-methylbenzenesulfonamide | 318.0752 |
| 17 | 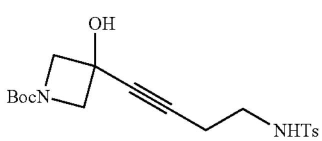 | tert-butyl 3-hydroxy-3-(4-((4-methylphenyl)sulfonamido)but-1-yn-1-yl)azetidine-1-carboxylate | 417.1402 |
| 18* | 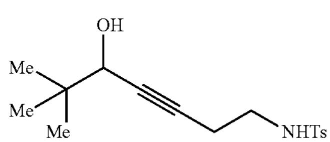 | N-(5-hydroxy-6,6-dimethylhept-3-yn-1-yl)-4-methylbenzenesulfonamide | 332.1272 |
| 19* | 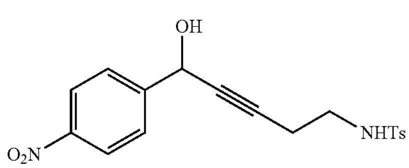 | N-(5-hydroxy-5-(4-nitrophenyl)pent-3-yn-1-yl)-4-methylbenzenesulfonamide | 397.0816 |
| 20* | 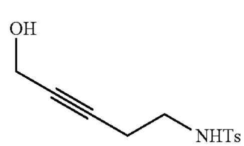 | N-(5-hydroxypent-3-yn-1-yl)-4-methylbenzenesulfonamide | 276.0623 |

TABLE 1-continued

Preparations 2-22 are prepared with essentially the same or similar method of preparing Preparation 1.

| Preparations | Structures | Chemical names | Physical Data [HRMS (ESI): m/z] [M + Na]+ |
|---|---|---|---|
| 21 | Ph—⟨structure with OH, alkyne, NHBoc⟩ | tert-butyl (5-hydroxy-7-phenylhept-3-yn-1-yl)carbamate | 326.1717 |
| 22 | Ph—⟨structure with OH, alkyne, NHTs⟩ | N-(6-hydroxy-8-phenyloct-4-yn-1-yl)-4-methylbenzenesulfonamide | 394.1378 |
| 23 | Me—⟨structure with OH, alkyne, NHTs⟩ | N-(6-hydroxynon-4-yn-1-yl)-4-methylbenzenesulfonamide | 332.1211 |

*The Preparations 18-20 are made from Boc-protected starting material and then treated with trifluoroacetic acid (TFA) to de-protect to provide the desired compounds.

EXAMPLES PREPARED BY PALLADIUM-CATALYZED CARBONYLATION

Example 1: 6-phenethyl-1-tosyl-1,2,3,6-tetrahydro-4H-furo[3,4-b]pyrrol-4-one

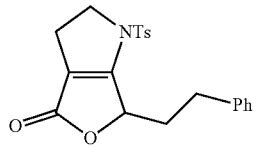 [SMILES: Cc1ccc(S(=O)(=O)N2CCC3=C2C(CCc2ccccc2)OC3=O)cc1]

Add Pd(MeCN)$_2$Cl2 (2.6 mg, 0.01 mmol), AgOTf (5.2 mg, 0.02 mmol) and ligand G (3.6 mg, 0.01 mmol) in dry MeCN (2 mL) and allowed to react for 1 h under argon atmosphere. Then add DDQ (34.1 mg, 0.15 mmol) and Preparation 1, which is N-(5-hydroxy-7-phenylhept-3-yn-1-yl)-4-methylbenzenesulfonamide (0.1 mmol), to the mixture, and the reaction was filled by CO balloon. The mixture was allowed to react at room temperature and the reaction was monitored by Thin Layer Chromatography (TLC) until no starting material was observed. The solvent was removed under reduced pressure and the residue was dissolved in CHCl$_3$ (1 mL). The crude product in CHCl$_3$ was purified by flash column chromatography (CHCl$_3$ then hexane/ethyl acetate=5/1) to give Example 1 in 90% yield. HRMS (ESI) [M+H]+: 384.1308 m/z.

TABLE 2

Examples 2-23 are prepared with essentially the same or similar method of preparing Example 1.

| Examples | Structures | Chemical names | Physical Data [HRMS (ESI): m/z] [M + H]+ |
|---|---|---|---|
| 2 | ⟨structure with NTs, lactone, ethyl-Me⟩ | 6-propyl-1-tosyl-1,2,3,6-tetrahydro-4H-furo[3,4-b]pyrrol-4-one | 322.1165 |
| 3 | ⟨structure with NTs, lactone, C(Me)$_3$⟩ | 6-(tert-butyl)-1-tosyl-1,2,3,6-tetrahydro-4H-furo[3,4-b]pyrrol-4-one | 336.1257 |

TABLE 2-continued

Examples 2-23 are prepared with essentially the same or similar method of preparing Example 1.

| Examples | Structures | Chemical names | Physical Data [HRMS (ESI): m/z)] [M + H]+ |
|---|---|---|---|
| 4 | 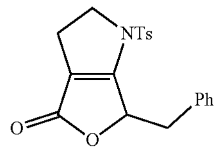 [SMILES: Cc1ccc(S(=O)(=O)N2CCC3=C2C(Cc2ccccc2)OC3=O)cc1] | 6-benzyl-1-tosyl-1,2,3,6-tetrahydro-4H-furo[3,4-b]pyrrol-4-one | 370.1098 |
| 5 | 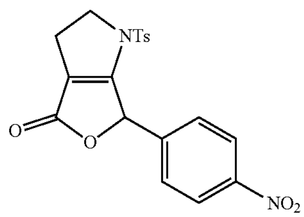 [SMILES: Cc1ccc(S(=O)(=O)N2CCC3=C2C(c2ccc([N+](=O)[O-])cc2)OC3=O)cc1] | 6-(4-nitrophenyl)-1-tosyl-1,2,3,6-tetrahydro-4H-furo[3,4-b]pyrrol-4-one | 401.0790 |
| 6 | 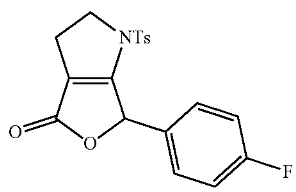 [SMILES: Cc1ccc(S(=O)(=O)N2CCC3=C2C(c2ccc(F)cc2)OC3=O)cc1] | 6-(4-fluorophenyl)-1-tosyl-1,2,3,6-tetrahydro-4H-furo[3,4-b]pyrrol-4-one | 374.0913 |
| 7 | 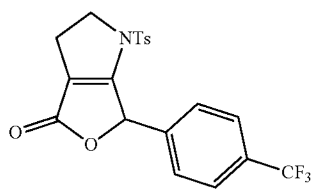 [SMILES: Cc1ccc(S(=O)(=O)N2CCC3=C2C(c2ccc(C(F)(F)F)cc2)OC3=O)cc1] | 1-tosyl-6-(4-(trifluoromethyl)phenyl)-1,2,3,6-tetrahydro-4H-furo[3,4-b]pyrrol-4-one | 424.0872 |
| 8 | 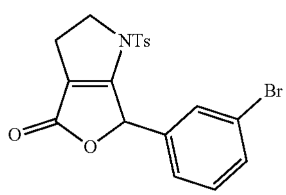 [SMILES: Cc1ccc(S(=O)(=O)N2CCC3=C2C(c2cccc(Br)c2)OC3=O)cc1] | 6-(3-bromophenyl)-1-tosyl-1,2,3,6-tetrahydro-4H-furo[3,4-b]pyrrol-4-one | 424.0040 |
| 9 | 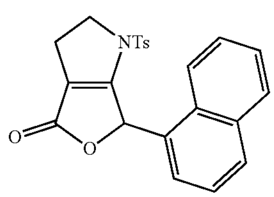 [SMILES: Cc1ccc(S(=O)(=O)N2CCC3=C2C(c2cccc4ccccc24)OC3=O)cc1] | 6-(naphthalen-1-yl)-1-tosyl-1,2,3,6-tetrahydro-4H-furo[3,4-b]pyrrol-4-one | 406.1110 |
| 10 | 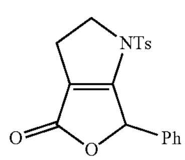 [SMILES: Cc1ccc(S(=O)(=O)N2CCC3=C2C(c2ccccc2)OC3=O)cc1] | 6-phenyl-1-tosyl-1,2,3,6-tetrahydro-4H-furo[3,4-b]pyrrol-4-one | 356.0963 |
| 11 | 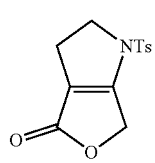 [SMILES: Cc1ccc(S(=O)(=O)N2CCC3=C2COC3=O)cc1] | 1-tosyl-1,2,3,6-tetrahydro-4H-furo[3,4-b]pyrrol-4-one | 280.0612 |

TABLE 2-continued

Examples 2-23 are prepared with essentially the same or similar method of preparing Example 1.

| Examples | Structures | Chemical names | Physical Data [HRMS (ESI): m/z)] [M + H]+ |
|---|---|---|---|
| 12 | 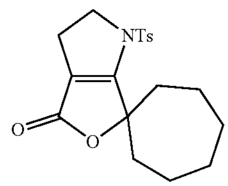 [SMILES: Cc1ccc(S(=O)(=O)N2CCC3=C2C2(CCCCCC2)OC3=O)cc1] | 1'-tosyl-2',3'-dihydrospiro[cycloheptane-1,6'-furo[3,4-b]pyrrol]-4'(1'H)-one | 362.1399 |
| 13 | 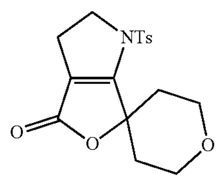 [SMILES: Cc1ccc(S(=O)(=O)N2CCC3=C2C2(CCOCC2)OC3=O)cc1] | 1-tosyl-2,2',3,3',5',6'-hexahydrospiro[furo[3,4-b]pyrrole-6,4'-pyran]-4(1H)-one | 350.1029 |
| 14 | 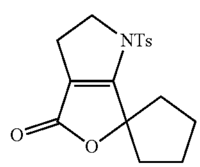 [SMILES: Cc1ccc(S(=O)(=O)N2CCC3=C2C2(CCCC2)OC3=O)cc1] | 1'-tosyl-2',3'-dihydrospiro[cyclopentane-1,6'-furo[3,4-b]pyrrol]-4'(1'H)-one | 334.1082 |
| 15 | 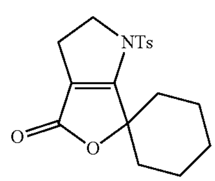 [SMILES: Cc1ccc(S(=O)(=O)N2CCC3=C2C2(CCCCC2)OC3=O)cc1] | 1'-tosyl-2',3'-dihydrospiro[cyclohexane-1,6'-furo[3,4-b]pyrrol]-4'(1'H)-one | 348.1230 |
| 16 | 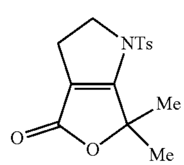 [SMILES: Cc1ccc(S(=O)(=O)N2CCC3=C2C(C)(C)OC3=O)cc1] | 6,6-dimethyl-1-tosyl-1,2,3,6-tetrahydro-4H-furo[3,4-b]pyrrol-4-one | 308.0969 |
| 17 | 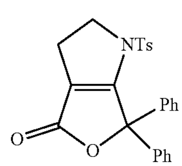 [SMILES: Cc1ccc(S(=O)(=O)N2CCC3=C2C(c2ccccc2)(c2ccccc2)OC3=O)cc1] | 6,6-diphenyl-1-tosyl-1,2,3,6-tetrahydro-4H-furo[3,4-b]pyrrol-4-one | 432.1238 |
| 18 | 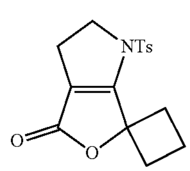 [SMILES: Cc1ccc(S(=O)(=O)N2CCC3=C2C2(CCC2)OC3=O)cc1] | 1'-tosyl-2',3'-dihydrospiro[cyclobutane-1,6'-furo[3,4-b]pyrrol]-4'(1'H)-one | 320.0955 |
| 19 | 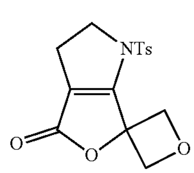 [SMILES: Cc1ccc(S(=O)(=O)N2CCC3=C2C2(COC2)OC3=O)cc1] | 1-tosyl-2,3-dihydrospiro[furo[3,4-b]pyrrole-6,3'-oxetan]-4(1H)-one | 322.0743 |

TABLE 2-continued

Examples 2-23 are prepared with essentially the same or similar method of preparing Example 1.

| Examples | Structures | Chemical names | Physical Data [HRMS (ESI): m/z)] [M + H]+ |
|---|---|---|---|
| 20 | 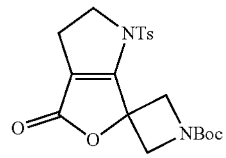 [SMILES: Cc1ccc(S(=O)(=O)N2CCC3=C2C2(CN(C(=O)OC(C)(C)C)C2)OC3=O)cc1] | tert-butyl 4'-oxo-1'-tosyl-1',2',3',4'-tetrahydrospiro[azetidine-3,6'-furo[3,4-b]pyrrole]-1-carboxylate | 431.1374 |
| 21 | 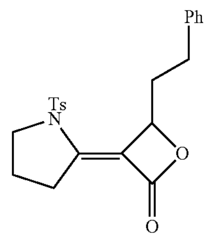 [SMILES: Cc1ccc(S(=O)(=O)N2CCC/C2=C2\C(=O)OC2CCc2ccccc2)cc1] | (E)-4-phenethyl-3-(1-tosylpyrrolidin-2-ylidene)oxetan-2-one | 398.1356 |
| 22 | 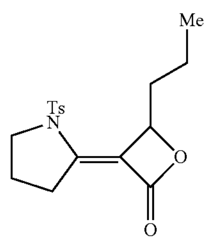 [SMILES: CCCC1OC(=O)/C1=C1\CCCN1S(=O)(=O)c1ccc(C)cc1] | (E)-4-propyl-3-(1-tosylpyrrolidin-2-ylidene)oxetan-2-one | 336.1236 |

Biological Evaluation

The broth microdilution assay was utilized to determine the minimum inhibitory concentration (MIC) of the Examples in the present disclosure against certain bacterial (Methicillin-resistant *Staphylococcus aureus* (MRSA), *Enterococcus faecium*, *Acinetobacter baumannii*, *Escherichia coli*, *Klebsiella pneumoniae*, *Pseudomonas aeruginosa* and *Clostridium difficile*) and fungal pathogens (*Candida albicans*, *Candida glabrata*, *Candida krusei*, *Cryptococcus gattii*, *Cryptococcus neoformans*, *Aspergillus fumigatus*, *Aspergillus niger*, and *Aspergillus brasiliensis*) following the guidelines of the Clinical and Laboratory Standards Institute.

Minimum Inhibitory Concentrations (MICs) Against *C. difficile* Strains

*Clostridium difficile* was grown anaerobically on brain heart infusion supplemented agar plates (Brain heart infusion medium, BD, supplemented with yeast extract, L-cysteine, Vitamin K1 and Hemin, Sigma) at 37° C. for 48 hours, afterwards a bacterial solution equivalent to 0.5 McFarland standard was prepared in PBS and diluted in brain heart infusion supplemented broth to achieve a bacterial concentration of about 5×10$^5$. Drugs were added at a concentration of 128 μM in the first row of a 96-well plates, 100 μL of the bacterial suspension was added to all the wells of the plates and two-fold serial dilution was done for each compound. See Institute CaLS. 2012. Methods for Dilution Antimicrobial Susceptibility Tests for Bacteria That Grow Aerobically—Ninth Edition: Approved Standard M07-A9, Wayne, Pa. Plates were then incubated at 37° C. anaerobically for 48 hours and examined for turbidity, MIC is considered the lowest concentration of a compound that can inhibit the development of visual turbidity.

Cytotoxicity Against Human Colorectal Adenocarcinoma Cell Line (Caco-2)

Examples were assayed at concentrations of 32, 64, 128, and 256 μM against human colorectal cancer-derived intestinal epithelial cell line (Caco-2) to determine the potential toxic effect on mammalian cells. About ×10$^4$ cells suspended in 100 μL of DMEM media (supplemented with 10% fetal bovine serum and 1% non-essential amino acids) were seeded in a 96-well plate and incubated at 37° C. in a 5% $CO_2$ atmosphere. After reaching confluency, cells were further incubated with the above mentioned concentrations of the compounds for 2 hours. The culture media were discarded, and the cells in each well were washed with media and 100 μL of cell culture media were added prior to addition of the assay reagent MTS 3-(4,5-dimethylthiazol-2-yl)-5-(3-carboxymethoxyphenyl)-2-(4-sulfophenyl)-2H-tetrazolium) (Promega). The plates were incubated for 4 hours at 37° C. in humidified 5% $CO_2$ atmosphere. The absorbance at 490 nm was recorded and corrected absorbance readings (actual absorbance readings for each treatment subtracted from background absorbance) were taken using a kinetic ELISA microplate reader (SpectraMax i3x, Molecular Devices, Sunnyvale, Calif., USA). The quantity of viable cells after treatment with each compound was expressed as a percentage of the control, DMSO. Statistical analysis was performed using two way ANOVA followed by Dunnett's pairwise comparison ($P<0.05$).

Antifungal Assay

Yeast and mold fungal suspensions were prepared and tested by broth microdilution method according to the guidelines of Clinical and Laboratory Standards Institute. See (CLSI) Clsi. 04/2008. Reference method for broth dilution antifungal susceptibility testing of yeast; approved standards-third edition (M27-A3). 28.

Compounds (tested from 128 μM down to 1 μM) were placed together in a 96 well-plate and incubated at 35° C. for 24 to 72 hours according to the strain tested. The MICs reported represent the lowest concentration of each compound necessary to inhibit bacterial growth Antibacterial Activities Examples 8 and 19 exhibited promising inhibitory activities of 64 μM to 128 μM minimum inhibitory concentrations (MIC) against toxigenic strains such as *C. difficile* P8, *C. difficile* BAA1870, *C. difficile* P 20, *C. difficile* P 7, and *C. difficile* P 21.

In addition, the toxicity study of Examples 8 and 19 against Caco-2 cell line demonstrated that neither compound showed toxicity up to 256 μM.

Antifungal Activities

Examples 8, 11, 19, and 22 exhibited promising inhibitory activities against certain fungal pathogens including strains of *Candida albicans, Candida glabrata, Candida krusei, Cryptococcus gattii, Cryptococcus neoformans, Aspergillus fumigatus, Aspergillus niger,* and *Aspergillus brasiliensis* with 64 μM to 128 μM minimum inhibitory concentrations.

Those skilled in the art will recognize that numerous modifications can be made to the specific implementations described above. The implementations should not be limited to the particular limitations described. Other implementations may be possible.

We claim:

1. A compound of formula (I)

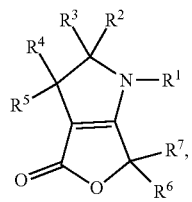

or any salt thereof, wherein $R^1$ is H, C1-C8 straight or branched alkyl, C3-C8 cycloalkyl, C6-C10 aryl, C4-C10 heteroaryl, hydroxyl, C1-C6 straight or branched alkoxyl, —C(X)—$R^{10}$, —C(X)—O$R^{11}$, —SO$_2$$R^{12}$, —C(X)N$R^{13}$$R^{14}$, or a nitrogen-protecting group, wherein the alkyl, aryl or heteroaryl is optionally substituted with one or more —NO$_2$, halogen, CF$_3$, or phenyl;

$R^2$, $R^3$, $R^4$, and $R^5$ are independently H, C1-C8 straight or branched alkyl, C3-C8 cycloalkyl, C6-C10 aryl, C4-C10 heteroaryl, hydroxyl, halogen, or C1-C6 straight or branched alkoxyl, wherein the alkyl, aryl or heteroaryl is optionally substituted with one or more —NO$_2$, halogen, CF$_3$, or phenyl;

$R^6$, $R^7$ are independently H, C1-C8 straight or branched alkyl, C3-C8 cycloalkyl, C6-C10 aryl, C4-C10 heteroaryl, C1-C6 straight or branched alkoxyl, wherein $R^6$, $R^7$ may form a C3-C10 carbon ring or heterocyclic ring comprising N, O, or S, and when the heterocyclic ring formed by $R^6$ and $R^7$ has N, the N is optionally attached to C1-C8 straight or branched alkyl, C3-C8 cycloalkyl, C6-C10 aryl, C4-C10 heteroaryl, —C(X)—$R^{10}$, —C(X)—O$R^{11}$, —SO$_2$$R^{12}$, —C(X)N$R^{13}$$R^{14}$, or a nitrogen-protecting group;

$R^{10}$-$R^{14}$ are independently H, C1-C8 straight or branched alkyl, C3-C8 cycloalkyl, C6-C10 aryl, C4-C10 heteroaryl, wherein the alkyl, aryl, or heteroaryl is optionally substituted with one or more C1-C4 straight or branched alkyl, —NO$_2$, halogen, or CF$_3$; and X is O or S.

2. The compound of claim 1, wherein the compound is made by a method comprises reacting a compound of formula A with carbon monoxide, a palladium catalyst, a ligand, and an oxidant in a solvent to provide the compound of formula I:

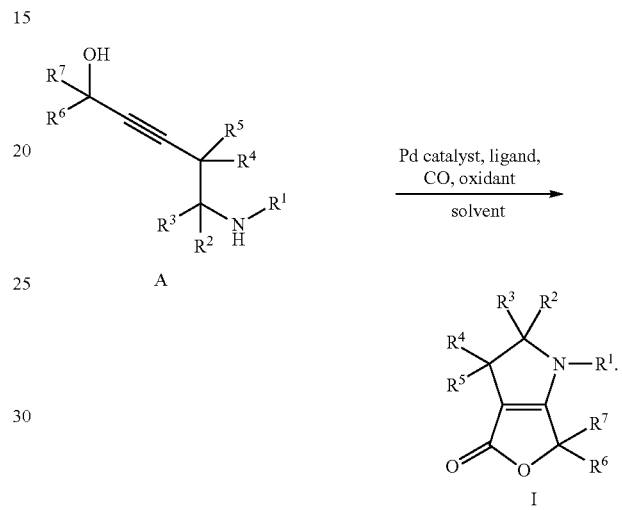

3. The compound of claim 1, wherein the compound is selected from the group consisting of:

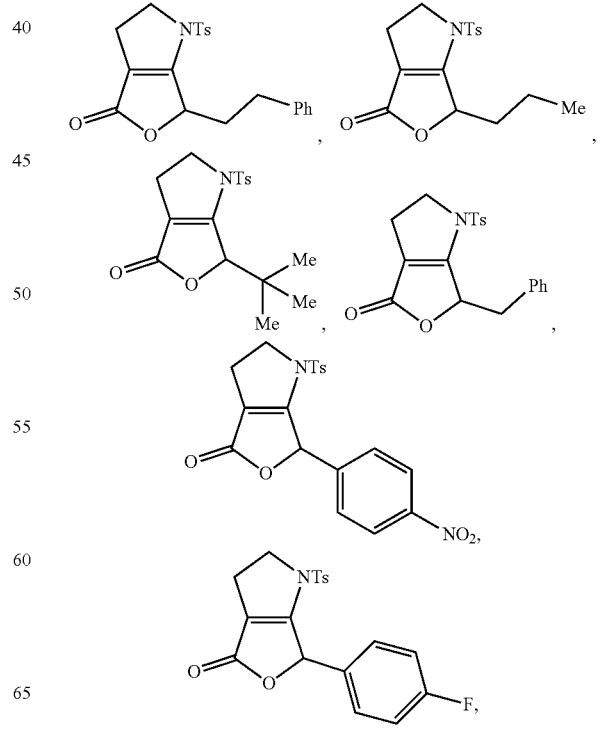

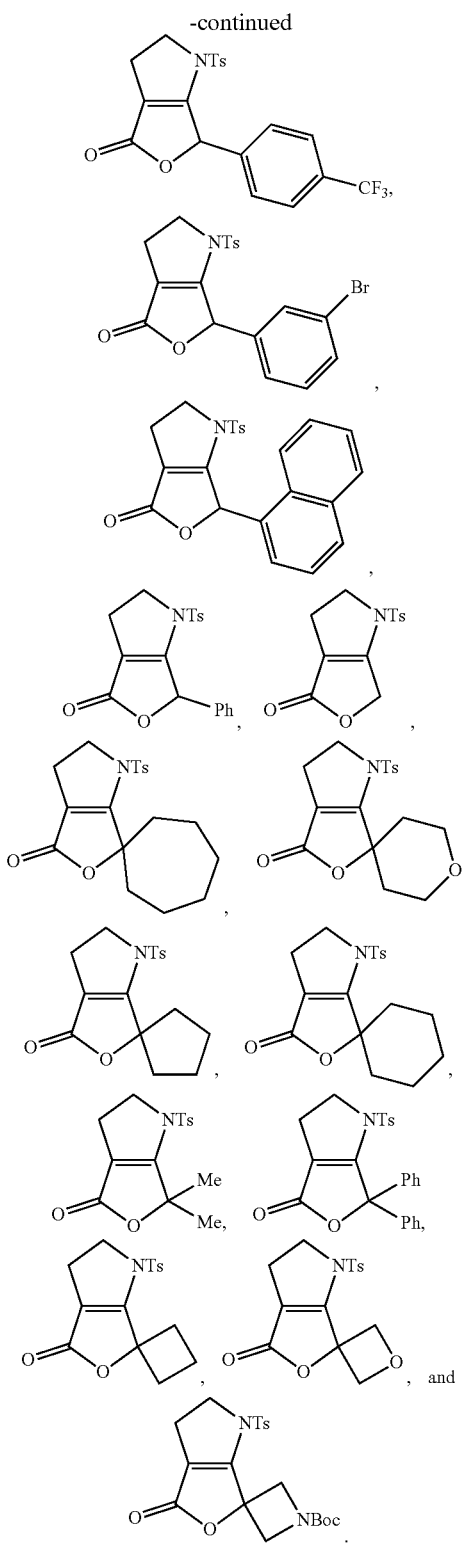

4. The compound of claim 1, wherein the compound is used as an anti-bacteria or anti-fungal agent.

5. A method of preparing the compound of formula (I) of claim 1, wherein the method comprises reacting a compound of formula A with carbon monoxide, a palladium catalyst, a ligand, and an oxidant in a solvent to provide the compound of formula I:

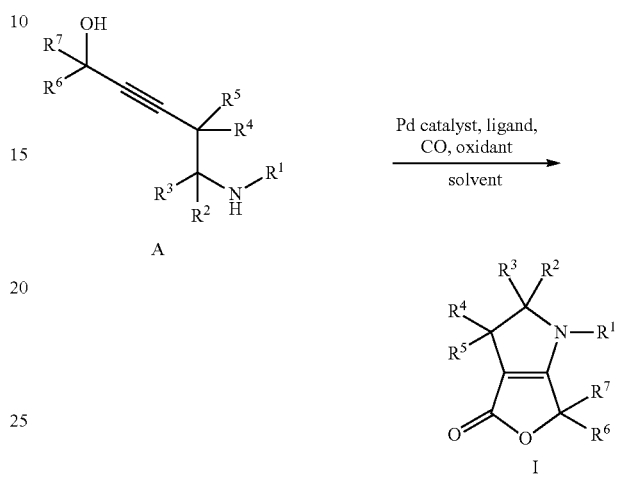

$R^1$ is H, C1-C8 straight or branched alkyl, C3-C8 cycloalkyl, C6-C10 aryl, C4-C10 heteroaryl, hydroxyl, C1-C6 straight or branched alkoxyl, —C(X)—$R^{10}$, —C(X)—$OR^{11}$, —$SO_2R^{12}$, —C(X)$NR^{13}R^{14}$, or a nitrogen-protecting group, wherein the alkyl, aryl or heteroaryl is optionally substituted with one or more —$NO_2$, halogen, $CF_3$, or phenyl;

$R^2$, $R^3$, $R^4$, and $R^5$ are independently H, C1-C8 straight or branched alkyl, C3-C8 cycloalkyl, C6-C10 aryl, C4-C10 heteroaryl, hydroxyl, halogen, or C1-C6 straight or branched alkoxyl, wherein the alkyl, aryl or heteroaryl is optionally substituted with one or more —$NO_2$, halogen, $CF_3$, or phenyl;

$R^6$, $R^7$ are independently H, C1-C8 straight or branched alkyl, C3-C8 cycloalkyl, C6-C10 aryl, C4-C10 heteroaryl, C1-C6 straight or branched alkoxyl, wherein $R^6$, $R^7$ may form a C3-C10 carbon ring or heterocyclic ring comprising N, O, or S, and when the heterocyclic formed by $R^6$ and $R^7$ has N, the N is optionally attached to C1-C8 straight or branched alkyl, C3-C8 cycloalkyl, C6-C10 aryl, C4-C10 heteroaryl, —C(X)—$R^{10}$, —C(X)—$OR^{11}$, —$SO_2R^{12}$, —C(X)$NR^{13}R^{14}$, or a nitrogen-protecting group;

$R^{10}$-$R^{14}$ are independently H, C1-C8 straight or branched alkyl, C3-C8 cycloalkyl, C6-C10 aryl, C4-C10 heteroaryl, wherein the alkyl, aryl, or heteroaryl is optionally substituted with one or more C1-C4 straight or branched alkyl, —$NO_3$, halogen, or $CF_3$; and X is O or S.

* * * * *